(12) United States Patent
Dahlqvist et al.

(10) Patent No.: US 9,834,355 B2
(45) Date of Patent: Dec. 5, 2017

(54) PACKAGING UNIT HAVING IMPROVED SEALING, AND A METHOD FOR FORMING SUCH A PACKAGING UNIT

(71) Applicant: SCA Hygiene Products AB, Göteborg (SE)

(72) Inventors: Conny Dahlqvist, Göteborg (SE); Ulrika Persson, Göteborg (SE); Sofia Ekstedt, Göteborg (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

(21) Appl. No.: 15/318,051

(22) PCT Filed: Jun. 13, 2014

(86) PCT No.: PCT/SE2014/050718
§ 371 (c)(1),
(2) Date: Dec. 12, 2016

(87) PCT Pub. No.: WO2015/190964
PCT Pub. Date: Dec. 17, 2015

(65) Prior Publication Data
US 2017/0129674 A1    May 11, 2017

(51) Int. Cl.
*A61B 17/06* (2006.01)
*B65D 75/20* (2006.01)
(Continued)

(52) U.S. Cl.
CPC ........ *B65D 75/20* (2013.01); *A61F 13/15747* (2013.01); *A61F 13/5514* (2013.01);
(Continued)

(58) Field of Classification Search
CPC .............. A61F 13/5514; A61F 13/5515; A61F 13/15747; B65D 65/14; B65D 75/20
(Continued)

(56) References Cited

U.S. PATENT DOCUMENTS 3,913,580 A    10/1975    Ginocchio
3,957,569 A    5/1976    Freitag
(Continued)

FOREIGN PATENT DOCUMENTS

EP    0 368 914 A1    5/1990
EP    0 841 049 A1    5/1998
(Continued)

OTHER PUBLICATIONS

Wikipedia, "Corona treatment", http://en.wikipedia.org/wiki/Corona_treatment, Mar. 16, 2015, 6 pages.
(Continued)

*Primary Examiner* — Luan K Bui
(74) *Attorney, Agent, or Firm* — Buchanan Ingersoll & Rooney PC

(57) ABSTRACT

A packaging unit for hygiene articles is formed from a sheet having a folding axis dividing the sheet into first and second regions. One of the inner edge portion and the outer edge portion of the edge zone of the first region is provided with resealable adhesive, thus forming a first adhesive zone. The other of the inner edge portion and the outer edge portion is adhesive-free. The inner edge portion or the outer edge portion of the edge zone of the second region corresponding to the adhesive-carrying edge portion of the first region is adhesive-free, such that when the sheet is folded about the folding axis, the edge portions carrying resealable adhesive in the first region are brought in contact with the adhesive-free edge portions in the second region. A distance between the at least one first folding axis and the first adhesive zone is 1-20 mm.

21 Claims, 2 Drawing Sheets

(51) Int. Cl.
- *A61F 13/551* (2006.01)
- *A61F 13/15* (2006.01)
- *B65D 65/14* (2006.01)
- *B65D 75/58* (2006.01)
- *B31B 160/10* (2017.01)
- *B31B 70/62* (2017.01)
- *B31B 150/00* (2017.01)

(52) U.S. Cl.
CPC .......... *A61F 13/5515* (2013.01); *B65D 65/14* (2013.01); *B65D 75/5855* (2013.01); *B31B 70/62* (2017.08); *B31B 2150/00* (2017.08); *B31B 2160/10* (2017.08); *B31B 2160/102* (2017.08); *B65D 2575/586* (2013.01)

(58) Field of Classification Search
USPC ........ 206/438, 440, 441, 494; 493/186, 243, 493/254, 264; 156/227, 289, 291, 441.5, 156/443; 229/69, 92.1, 300, 305; 604/385.02, 385.05
See application file for complete search history.

(56) References Cited

U.S. PATENT DOCUMENTS

| | | | |
|---|---|---|---|
| 5,167,739 A * | 12/1992 | Hutchinson | B42D 15/08 156/291 |
| 5,238,178 A * | 8/1993 | Hutchinson | B42C 3/00 229/314 |
| 5,375,764 A * | 12/1994 | Sauerwine | B65D 27/04 229/304 |
| H1454 H | 6/1995 | Cucuzza et al. | |
| 5,462,166 A | 10/1995 | Minton et al. | |
| 5,567,260 A | 10/1996 | McFall | |
| 5,569,230 A | 10/1996 | Fisher et al. | |
| 5,591,153 A | 1/1997 | Mattingly, III | |
| 5,598,970 A * | 2/1997 | Mudry | B65D 27/06 229/300 |
| 5,769,837 A | 6/1998 | Parr | |
| 5,792,131 A | 8/1998 | Mizutani | |
| 5,868,727 A | 2/1999 | Barr et al. | |
| 6,003,760 A * | 12/1999 | Abercrombie | B42D 15/08 229/305 |
| 6,015,934 A | 1/2000 | Lee et al. | |
| 6,039,242 A * | 3/2000 | Tee | B42D 15/08 229/92.1 |
| 6,176,850 B1 | 1/2001 | Rosenfeld et al. | |
| 6,203,512 B1 | 3/2001 | Farris et al. | |
| 6,234,229 B1 | 5/2001 | Tabuchi | |
| 6,322,106 B1 * | 11/2001 | Mehta | B65D 27/06 229/301 |
| 7,083,079 B2 * | 8/2006 | Bethke | B42D 5/026 229/300 |
| 7,708,727 B2 | 5/2010 | Woltman et al. | |
| 8,231,590 B2 | 7/2012 | Zander et al. | |
| 8,900,210 B2 | 12/2014 | Drevik et al. | |
| 2003/0163109 A1 | 8/2003 | Ohba et al. | |
| 2003/0225390 A1 | 12/2003 | Vogt et al. | |
| 2003/0234069 A1 | 12/2003 | Coenen et al. | |
| 2004/0107676 A1 | 6/2004 | Murray | |
| 2005/0137553 A1 | 6/2005 | Bechyne et al. | |
| 2005/0198931 A1 | 9/2005 | Cesiro et al. | |
| 2006/0025739 A1* | 2/2006 | DiPalma | A61F 13/5513 604/385.02 |
| 2006/0137568 A1 | 6/2006 | MacDonald et al. | |
| 2007/0049891 A1 | 3/2007 | Clark, Jr. et al. | |
| 2007/0189644 A1 | 8/2007 | Murray | |
| 2008/0067803 A1 | 3/2008 | Tanigawa | |
| 2009/0082747 A1 | 3/2009 | Carlen et al. | |
| 2010/0175825 A1 | 7/2010 | Baldauf | |
| 2010/0298797 A1 | 11/2010 | Ehlenbach et al. | |
| 2011/0028933 A1 | 2/2011 | Fung et al. | |
| 2011/0034897 A1 | 2/2011 | Nomoto et al. | |
| 2012/0090071 A1 | 4/2012 | Umebayashi | |
| 2012/0283682 A1 | 11/2012 | Otsubo et al. | |
| 2013/0165888 A1 | 6/2013 | Kinoshita et al. | |
| 2013/0199956 A1 | 8/2013 | Hunter et al. | |
| 2014/0155852 A1 | 6/2014 | Nishimura et al. | |
| 2015/0112294 A1 | 4/2015 | Dahl et al. | |

FOREIGN PATENT DOCUMENTS

| | | |
|---|---|---|
| EP | 0 955 243 A2 | 11/1999 |
| EP | 2 589 356 A1 | 5/2013 |
| EP | 2 737 886 A1 | 6/2014 |
| GB | 2 273 279 A | 6/1994 |
| JP | 2003-199786 A | 7/2003 |
| JP | 2006-45417 A | 2/2006 |
| JP | 2009-73498 A | 4/2009 |
| JP | 2013-85818 A | 5/2013 |
| WO | WO 88/10219 A1 | 12/1988 |
| WO | WO 89/00459 A1 | 1/1989 |
| WO | WO 95/00092 A1 | 1/1995 |
| WO | WO 97/34556 A2 | 9/1997 |
| WO | WO 00/45767 A1 | 8/2000 |
| WO | WO 03/030796 A1 | 4/2003 |
| WO | WO 2005/087167 A1 | 9/2005 |
| WO | WO 2010/071512 A1 | 6/2010 |
| WO | WO 2010/135566 A1 | 11/2010 |
| WO | WO 2012/102071 A1 | 8/2012 |
| WO | WO 2012/157621 A1 | 11/2012 |
| WO | WO 2013/162430 A1 | 10/2013 |
| WO | WO 2014/188239 A1 | 11/2014 |

OTHER PUBLICATIONS

International Search Report (PCT/ISA/210) dated Feb. 23, 2015, by the Swedish Patent Office as the International Searching Authority for International Application No. PCT/SE2014/050724.
Written Opinion (PCT/ISA/237) dated Feb. 23, 2015, by the Swedish Patent Office as the International Searching Authority for International Application No. PCT/SE2014/050724.
International Preliminary Report on Patentability (PCT/IPEA/409) dated Jun. 8, 2016, by the Swedish Patent Office as the International Searching Authority for International Application No. PCT/SE2014/050724.
International Search Report (PCT/ISA/210) dated Feb. 20, 2015, by the Swedish Patent Office as the International Searching Authority for International Application No. PCT/SE2014/050725.
Written Opinion (PCT/ISA/237) dated Feb. 20, 2015, by the Swedish Patent Office as the International Searching Authority for International Application No. PCT/SE2014/050725.
International Preliminary Report on Patentability (PCT/IPEA/409) dated Jun. 13, 2016, by the Swedish Patent Office as the International Searching Authority for International Application No. PCT/SE2014/050725.
International Search Report (PCT/ISA/210) dated Feb. 16, 2015, by the Swedish Patent Office as the International Searching Authority for International Application No. PCT/SE2014/050719.
Written Opinion (PCT/ISA/237) dated Feb. 16, 2015, by the Swedish Patent Office as the International Searching Authority for International Application No. PCT/SE2014/050719.
International Preliminary Report on Patentability (PCT/IPEA/409) dated Jun. 14, 2016, by the Swedish Patent Office as the International Searching Authority for International Application No. PCT/SE2014/050719.
European Patent Office Letter dated Mar. 27, 2015, for International Application No. PCT/SE2014/050719.
International Search Report (PCT/ISA/210) dated Feb. 11, 2015, by the Swedish Patent Office as the International Searching Authority for International Application No. PCT/SE2014/050720.
Written Opinion (PCT/ISA/237) dated Feb. 11, 2015, by the Swedish Patent Office as the International Searching Authority for International Application No. PCT/SE2014/050720.
Written Opinion of the International Preliminary Examining Authority (PCT/IPEA/408) dated Jun. 3, 2016, by the Swedish Patent Office as the International Searching Authority for International Application No. PCT/SE2014/050720.

(56) References Cited

OTHER PUBLICATIONS

Written Opinion of the International Preliminary Examining Authority (PCT/IPEA/408) dated Jul. 7, 2016, by the Swedish Patent Office as the International Searching Authority for International Application No. PCT/SE2014/050720.
European Patent Office Letter dated Aug. 24, 2015, for International Application No. PCT/SE2014/050720.
European Patent Office Letter dated Jun. 29, 2016, for International Application No. PCT/SE2014/050720.
International Search Report (PCT/ISA/210) dated Mar. 2, 2015, by the Swedish Patent Office as the International Searching Authority for International Application No. PCT/SE2014/050726.
Written Opinion (PCT/ISA/237) dated Mar. 2, 2015, by the Swedish Patent Office as the International Searching Authority for International Application No. PCT/SE2014/050726.
Written Opinion of the International Preliminary Examining Authority (PCT/IPEA/408) dated Jun. 3, 2016, by the Swedish Patent Office as the International Searching Authority for International Application No. PCT/SE2014/050726.
International Preliminary Report on Patentability (PCT/IPEA/409) dated Jul. 12, 2016, by the Swedish Patent Office as the International Searching Authority for International Application No. PCT/SE2014/050726.
European Patent Office Letter dated Apr. 7, 2015, for International Application No. PCT/SE2014/050726.
International Search Report (PCT/ISA/210) dated Feb. 11, 2015, by the Swedish Patent Office as the International Searching Authority for International Application No. PCT/SE2014/050718.
International Preliminary Report on Patentability (PCT/IPEA/409) dated Jun. 8, 2016, by the Swedish Patent Office as the International Searching Authority for International Application No. PCT/SE2014/050718.
European Patent Office Letter dated Mar. 27, 2015, for International Application No. PCT/SE2014/050718.
Office Action (Examination Report No. 1 for Standard Patent Application) dated Feb. 13, 2017, by the Australian Patent Office in corresponding Australian Patent Application No. 2014396900. (3 pages).
Ciba-Geigy AG (Durr's) Applications [1977] RPC 83. Published Feb. 17, 1977.
Section 2.9.2.8 of Australian Patent Manual of Practice & Procedure, titled "Printed Matter". Retrieved Feb. 19, 2017. <http://manuals.ipaustralia.gov.au/patents/national/patentable/2.9.2.8_printed_matter.htm>. (2 pages).

* cited by examiner

PACKAGING UNIT HAVING IMPROVED SEALING, AND A METHOD FOR FORMING SUCH A PACKAGING UNIT

TECHNICAL FIELD

The present disclosure relates to a packaging unit for hygiene articles, wherein the packaging unit provides a tightly sealed package both when packaging a new and disposing of a used hygiene article. The present disclosure further relates to a method for forming a packaging unit.

BACKGROUND

Disposable hygiene articles, such as sanitary napkins and panty liners, are normally packaged individually in e.g. an easy wrap or a single wrap. Individual packages facilitate hygienic carrying of single articles for future use, e.g. in a handbag. The edges of the individual packages are often sealed by means of ultrasonic welding or heat welding. Further, the packaging units are often used both as a means for packaging an unused article and for disposal of the used article.

It is desirable that used articles of this kind can be disposed of discretely and hygienically. This may be particularly important when the user lacks the possibility to dispose of the used article immediately after the used article has been replaced, e.g. when there is no waste bin available in the toilet area. In this case, the user may need to put the used article in e.g. her handbag or backpack, which requires the package to be adequately sealed in order to avoid staining and odour.

One solution addressing the disposal problem has been suggested in WO 2013/162430, describing a packaging unit being formed from a sheet having at least one folding axis dividing the sheet into a first region and a second region. The inner surface of the first region comprises an inner edge portion and an outer edge portion, wherein one of the portions is provided with adhesive, and the other of the portions is adhesive-free. Further, one of the inner and outer edge portions of the second region is either provided with adhesive or is adhesive-free in a complementary manner to the first region. Thus, when the sheet is folded about the folding axis, the edge portions carrying adhesive in the first region are brought in contact with the adhesive-free edge portions in the second region, and the edge portions carrying adhesive in the second region are brought in contact with the adhesive-free edge portions in the first region. The packaging unit disclosed in WO 2013/162430 provides an improved sealing both when packaging a new hygiene article, and when the packaging unit is used for disposal of a soiled hygiene article.

However, it has been shown that the manufacturing process of a packaging unit described in WO 2013/162430 may be adversely affected by the presence of adhesive-carrying edge portions. For instance, during the folding step, the adhesive arranged at the edge portions of the packaging unit may be caught by the folding tool, which will either cause a transfer of the adhesive from the packaging unit to the tool, or will lead to an inaccurate folding. In both cases, manufacturing of the packaging unit will be impaired.

Hence, there is a need for a packaging unit which can be used both for packaging a new hygiene article and for hygienic keeping and disposal of the used hygiene article, which is aesthetically appealing and which facilitates manufacturing.

SUMMARY

The present disclosure provides a packaging unit for hygiene articles and a method of forming a packaging unit, which substantially eliminates the drawbacks of the packaging units discussed above.

The present disclosure provides a packaging unit providing a possibility of forming a tight package both for a new and a used article, thus keeping the new article sanitary and clean prior to use, and eliminating the risk of staining and odour when a used article is packaged. The packaging unit is easy to unfold and reseal and is aesthetically appealing. Further, the packaging unit according to the present disclosure facilitates manufacturing.

As used herein, the term "inner surface" refers to the surface of the packaging unit facing the product positioned inside the packaging unit, and the term "outer surface" refers to the surface opposite to the inner surface, i.e. the surface facing the ambient.

By the term "edge zone" is meant the portion of the packaging unit adjacent to the edges of the packaging unit. The width of an edge zone may be varied.

The term "inner edge portion" refers to the portion of the edge zone positioned towards the centreline of the packaging unit.

The term "outer edge portion" refers to the portion of the edge zone positioned towards the edge of the packaging unit.

By the term "single ply" is meant a packaging unit comprising a single ply of a coherent material. The examples of a single ply packaging unit may be a plastic film, such as a polyethylene film, a nonwoven material, a metallic foil or the like. A single ply material may be a non-homogenous material such as a plastic film material comprising integrated layers, or a nonwoven material having varying fibre composition in different parts of the material. A single ply material as used herein does not comprise materials having separable layers.

By the term "laminate" is meant a packaging unit comprising at least two united separable plies of material that can be the same or different. In the context of the present disclosure, the laminate may for example be constituted of two separable plies of plastic film, a film and nonwoven, two plies of nonwoven or the like.

By the term "resealable adhesive" is meant an adhesive that provides a non-permanent adhesive bond between two adherent surfaces, i.e. a bond that may be broken by applying a pulling force to the adherent, and recreated by applying a pressing force to the adherent.

The packaging unit for hygiene articles according to the present disclosure is formed from a sheet of material having an inner surface and an outer surface. The inner surface comprises an edge zone comprising an inner edge portion and an outer edge portion. The packaging unit has at least one first folding axis dividing the sheet into a first region and a second region. One of the inner edge portion and the outer edge portion of the edge zone of the first region is provided with resealable adhesive, thus forming a first adhesive zone, and the other of the inner edge portion and the outer edge portion of the edge zone of the first region is adhesive-free. Further, the inner edge portion or the outer edge portion of the edge zone of the second region corresponding to the adhesive-carrying edge portion of the first region is adhesive-free, such that when the sheet is folded about the first folding axis, the edge portions carrying resealable adhesive in the first region are brought in contact with the adhesive-free edge portions in the second region. The distance between the at least one first folding axis and the first adhesive zone is 1-20 mm, preferably 2-18 mm, more preferably 3-15 mm.

Providing such a distance between the first folding axis and the first adhesive zone creates an adhesive-free portion between the first folding axis and the first adhesive zone. Thus, a folding tool may be positioned at the first folding axis without the risk of being caught by the resealable adhesive arranged at the first adhesive zone.

The distance between the first folding axis and the first adhesive zone may be varied depending on the dimensions of the packaging unit, and the size of the edge zones. Also, the distance between the first folding axis and the first adhesive zone should be optimized such that it provides sufficient space for the folding tool, while still providing a possibility of forming a sufficiently tightly sealed package around both a new and a used article.

A suitable resealable adhesive to be used with the packaging unit of the present disclosure is pressure-sensitive adhesive having an unlimited open time, meaning that the adhesive can bond to another substrate at any time.

The resealable adhesive used with the packaging unit is one which has a very high self-adhesion but which can be readily separated or released from other materials, such as plastic materials or paper which has been treated with a release agent. A major advantage of the packaging unit according to the present disclosure is that it can be completely unfolded when a new hygiene article is about to be taken out. In contrast thereto, prior art packages having adhesively sealed edges with adhesive-coated edge portions being in contact with each other have too high adhesive strength of the adhesively sealed edges, and any attempt to completely unfold the package generally leads to tearing and breakage of the packaging unit, making it unusable for discrete and hygienic disposal of the used article. As the adhesive-coated edge portions of the packaging unit of the present disclosure are not in contact with each other when the packaging unit is folded, the packaging unit can be readily opened and resealed, providing a tight disposal package. At the same time, the tensile strength of the adhesively sealed edges of the packaging unit using the adhesive pattern of the present disclosure is sufficient to provide a tight package for both a new and a used article, and low enough to provide a readily-opened package.

The geometrical shape of the sheet can vary depending on the type of the hygiene article to be packaged. The sheet may be circular, triangular, square, rectangular, or any other shape suitable for the hygiene article to be packaged. It is desirable, however, that the sheet has at least one symmetry axis.

In the packaging unit according to the present disclosure, one of the inner edge portion and the outer edge portion of the edge zone of the second region complementary to the adhesive-carrying edge portion of the first region may be adhesive-free. In other words, the edge zone of the second region, i.e. both the inner and outer edge portions of the second region, may be adhesive-free. In such an embodiment, the package is sealed by means of the resealable adhesive provided at the first adhesive zone, which has the advantage of minimizing the consumption of the resealable adhesive. On the other hand, the width of the first adhesive zone should be sufficient in order to provide an adequate sealing strength.

According to another embodiment, one of the inner edge portion and the outer edge portion of the edge zone of the second region complementary to the adhesive-carrying edge portion of the first region may be provided with resealable adhesive, thus forming a second adhesive zone. In such an embodiment, when the packaging unit is folded about the first folding axis, the edge portions carrying resealable adhesive in the first region are brought in contact with the adhesive-free edge portions in the second region, and the edge portions carrying resealable adhesive in the second region are brought in contact with the adhesive-free edge portions in the first region.

If the distance between the first folding axis and the first adhesive zone is sufficiently large to allow a folding tool to be positioned at the first folding axis without the risk of the folding tool being caught by the resealable adhesive of the second adhesive zone, the longitudinal extension of the second adhesive zone may be equal to the longitudinal extension of the second region. Preferably, the distance between the first folding axis and the second adhesive zone is 1-20 mm, preferably 2-18 mm, more preferably 3-15 mm, such that a space for positioning a folding tool is created on either side of the first folding axis. The distance between the first folding axis and the first adhesive zone and the distance between the first folding axis and the second adhesive zone may be the same or different.

As mentioned above, the packaging unit comprises at least one first folding axis. The number of folding axes may vary depending on how the packaging unit is intended to be folded. It is preferred that the packaging unit comprises between one and three folding axes.

The prevailing shape of the sheet of material for forming a packaging unit is square or rectangular. Such a sheet according to the present disclosure has side edges, referred to herein as longitudinal edges, a first and a second transverse edge and corner portions, the edge zones of the first and second regions of the sheet of material being arranged along the longitudinal edges. The edge portions covered with resealable adhesive and adhesive-free edge portions are thus positioned along the longitudinal edges. Preferably, the resealable adhesive arranged at the outer edge portions is positioned such that it extends all the way to the longitudinal edges of the sheet.

The width of the adhesive-covered edge portions may be varied depending on the adhesive strength desired. The wider the adhesive-covered edge zones, the stronger the sealing. The width of the adhesive-covered edge portions may be same or different in the different regions.

The sheet of material may comprise a first and a second transverse edge zones, being arranged along the transverse edges of the sheet of material from which the packaging unit according to the present disclosure is formed. The first transverse edge zone is provided at the transverse edge of the first region. The positioning of the second transverse edge zone depends on the number of folding axes. When the wrapping sheet comprises one folding axis, the second transverse edge zone is arranged at the transverse edge of the second region. When the wrapping sheet comprises two folding axes, the second transverse edge zone is arranged at the transverse edge of the third region, and so forth.

Preferably, the first transverse edge zone of the first region of the packaging unit is provided with the resealable adhesive, while the second transverse edge zone of the wrapping sheet is adhesive-free. When the wrapping sheet comprises one folding axis, it is conceivable that a portion of the first transverse edge zone of the first region is provided with the first resealable adhesive, while the remaining portion of the first transverse edge zone of the first region is adhesive-free, and a portion of the second transverse edge zone of the second region is provided with the first adhesive, while a remaining portion of the second transverse edge zone of the second region is adhesive-free in a complementary manner to the transverse edge zone of the first region. Thus, when the packaging unit is folded about the first folding axis, the transverse edge portion carrying the resealable adhesive in the first region is brought in contact with the adhesive-free transverse edge portion in the second region, and the transverse edge portion carrying the first resealable adhesive in the second region is brought in contact with the adhesive-free transverse edge portion in the first region. Also, both the first and the second transverse edge zones of the packaging unit may be provided with the resealable adhesive, when the packaging unit comprises at least two folding axes.

In order to facilitate opening, at least one of the corner portions may be free from resealable adhesive such that a gripping tab is formed.

As mentioned above, one of the most common folding patterns for individually wrapped hygiene products is so called e-folding. In this case the sheet has a first and a second folding axis, dividing the sheet into the first region, the second region and a third region. The packaging unit may then be formed, wherein the sheet is folded along the folding axes with the first, second and third regions in an overlapping configuration.

In order to obtain a tight package both when packaging a new hygiene article and when forming a disposal package for a used hygiene article, one of the inner and outer edge portions of the edge zone of the third region may be provided with resealable adhesive, thus forming a third adhesive zone.

The third adhesive zone may be positioned either at the inner or the outer edge portion of the edge zone of the third region. Thus, the third adhesive zone may be positioned at the edge portion of the third region being either complementary or corresponding to the edge portion comprising the first adhesive zone.

When the second region comprises the second adhesive zone arranged at the edge portion being complementary to the edge portion of the first region being provided with resealable adhesive, and the third adhesive zone is provided at the edge portion of the third region corresponding to the edge portion of the first region being provided with resealable adhesive, and complementary to the positioning of the second adhesive zone, a chessboard pattern of resealable adhesive is formed along each of the longitudinal edge zones. In such an embodiment, folding of the packaging unit may be initiated around either of the first and the second folding axes.

When the second region comprises the second adhesive zone arranged at the edge portion being complementary to the edge portion of the first region being provided with resealable adhesive, and the third adhesive zone is provided at the edge portion of the third region corresponding to the edge portion of the second region being provided with resealable adhesive, and complementary to the positioning of the first adhesive zone, folding of the package containing a new hygiene article is initiated around the first folding axis, such that the adhesive-covered edge portions of the first region are brought into contact with the adhesive-free portions of the second region, and the adhesive-covered portions of the second region are brought into contact with the adhesive-free portions of the first region. Subsequent folding around the second folding axis brings the inner surface of the third region into contact with the outer surface of the first region, thus forming a lid and sealing the package. When the packaging unit according to such an embodiment is used for disposal of a soiled article, folding of the packaging unit may be initiated around either of the first and the second folding axes, since when the packaging unit is used for disposal, it is no longer a requirement to maintain reclosability of the packaging unit.

When the second region comprises the second adhesive zone arranged at the edge portion being complementary to the edge portion of the first region being provided with resealable adhesive, the edge portion of the third region may be adhesive-free. In such an embodiment, folding of the packaging unit is initiated around the second folding axis, such that the adhesive-covered edge portions of the second region are brought into contact with the adhesive-free portions of the third region. Subsequent folding around the first folding axis brings the adhesive-covered edge portions of the first region into contact with the outer surface of the third region of the packaging unit, thus forming a sealed package.

When the second region comprises the second adhesive zone, the distance between the second folding axis and the second adhesive zone may be 1-20 mm, preferably 2-18 mm, more preferably 3-15 mm.

When the edge portion of the second region is adhesive-free, one of the inner and the outer edge portion of the third region is provided with resealable adhesive, thus forming the third adhesive zone. The third adhesive zone may be positioned at the edge portion of the third region being either complementary or corresponding to the edge portion of the first region comprising the first adhesive zone. In such an embodiment, folding of the packaging unit may be initiated around either of the first and the second folding axes.

Preferably, the distance between the second folding axis and the third adhesive zone may be 1-20 mm, preferably 2-18 mm, more preferably 3-15 mm, such that a space for positioning a folding tool is created on either side of the second folding axis. The distance between the second folding axis and the second adhesive zone and the distance between the second folding axis and the third adhesive zone may be same or different.

At least a portion of at least one of the transverse edge zones of the packaging unit comprising two folding axes may be provided with resealable adhesive, as mentioned above. Preferably, the transverse edge zone of one of the first or the third region is provided with resealable adhesive. In such an embodiment, folding should be initiated around the folding axis being adjacent to the region of the packaging unit comprising the adhesive-free transverse edge zone, such that the inner surface of the region comprising the adhesive-carrying transverse edge zone is brought into contact with the outer surface of the region comprising the adhesive-free transverse edge zone, thus forming a sufficiently tightly sealed package.

The sheet for forming a packaging unit may be a single ply sheet of any suitable material known to the person skilled in the art, such as polyethylene film or nonwoven. The sheet may also be a laminate comprising at least two distinct layers. Laminates suitable for packaging of hygiene articles are assumed to be known to the person skilled in the art, and are not in any way limiting for the present disclosure.

If desired, the sheet for forming a packaging unit according to the present disclosure may be opaque in order to disguise the contents of the packaging unit, which is particularly important if the used article wrapped into the packaging unit of the present disclosure cannot be disposed of immediately after replacement. Further, the sheet may comprise print, which may be beneficial for attracting the user's attention and improving the user's mood.

The sheet of material forming a packaging unit according to the present disclosure may comprise an odour-inhibiting or odour-neutralising substance. Such a substance may be applied in any suitable manner known to the person skilled in the art, e.g. as a coating, activatable microcapsules, impregnated patches, or the like.

It is conceivable that the sheet for forming a packaging unit according to the present disclosure may be stretchable or expandable, which may be advantageous if the hygiene article is greatly deformed during use, and may thus be difficult to wrap without deforming the packaging unit.

The resealable adhesive used in the present disclosure may be a pressure-sensitive hotmelt adhesive, such as Lunatack® D656 BD 19 available from H. B. Fuller.

It should be noted that when the packaging unit according to the present disclosure is used for disposal, the user may choose to roll up the packaging unit instead of folding, regardless of the adhesive pattern at the edge zone of the packaging unit.

The packaging unit according to the present disclosure may be manufactured by a method comprising the steps of:
  providing a sheet having an inner surface and an outer surface, the inner surface comprising an edge zone comprising an inner edge portion and an outer edge portion, the sheet having at least one first folding axis, the first folding axis dividing the sheet into a first region and a second region;
  providing one of the inner edge portion and the outer edge portion of the edge zone of the first region with resealable adhesive, such that the other of the inner edge portion and the outer edge portion of the edge zone of the first region is adhesive-free, thus forming a first adhesive zone; wherein the inner edge portion or the outer edge portion of the edge zone of the second region corresponding to the adhesive-carrying edge portion of the first region is adhesive-free; and such that a distance between the at least one first folding axis and the first adhesive zone is 1-20 mm, preferably 2-18 mm, more preferably 3-15 mm;
  folding the sheet about the folding axis, such that the edge portions carrying resealable adhesive in the first region are brought in contact with the adhesive-free edge portions in the second region.

The method may further comprise the step of:
  providing one of the inner edge portion and the outer edge portion of the edge zone of the second region complementary to the adhesive-carrying edge portion of the first region with resealable adhesive, thus forming a second adhesive zone.

As mentioned above, the second adhesive zone may be provided such that a distance between the second adhesive zone and the first folding axis is 1-20 mm, preferably 2-18 mm, more preferably 3-15 mm, in order to provide a sufficient space for positioning a folding tool at the first folding axis, and minimizing the risk of the folding tool being caught by the resealable adhesive arranged at the edge zone.

When the sheet has a first and a second folding axis dividing the sheet into the first region, the second region and a third region, the method may further comprise the steps of:
  providing one of said inner and said outer portions of the edge zone of the third region with resealable adhesive, thus forming a third adhesive zone;
  folding the sheet such that the first, second and third regions are arranged in an overlapping configuration.

As mentioned above, the third adhesive zone may be provided such that a distance between the third adhesive zone and the second folding axis is 1-20 mm, preferably 2-18 mm, more preferably 3-15 mm, in order to provide a sufficient space for positioning a folding tool at the second folding axis, and minimizing the risk of the folding tool being caught by the resealable adhesive arranged at the edge zone.

BRIEF DESCRIPTION OF THE DRAWINGS

Embodiments of the present disclosure will now be described by way of example with reference to the accompanying drawings, of which.

DETAILED DESCRIPTION OF PREFERRED EMBODIMENTS

Figure 1:
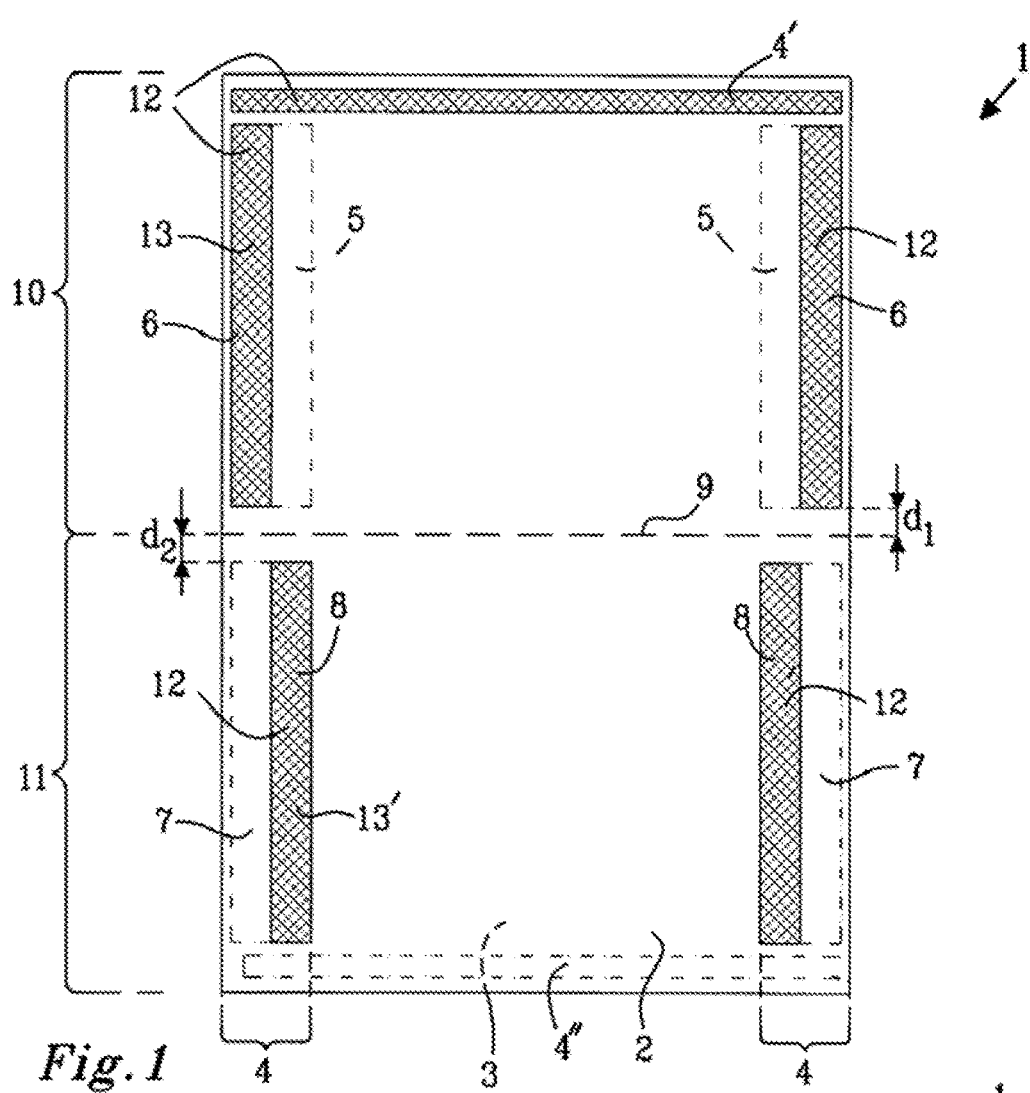
FIG. 1 shows a packaging unit according to an embodiment having one folding axis.
Figure 2:
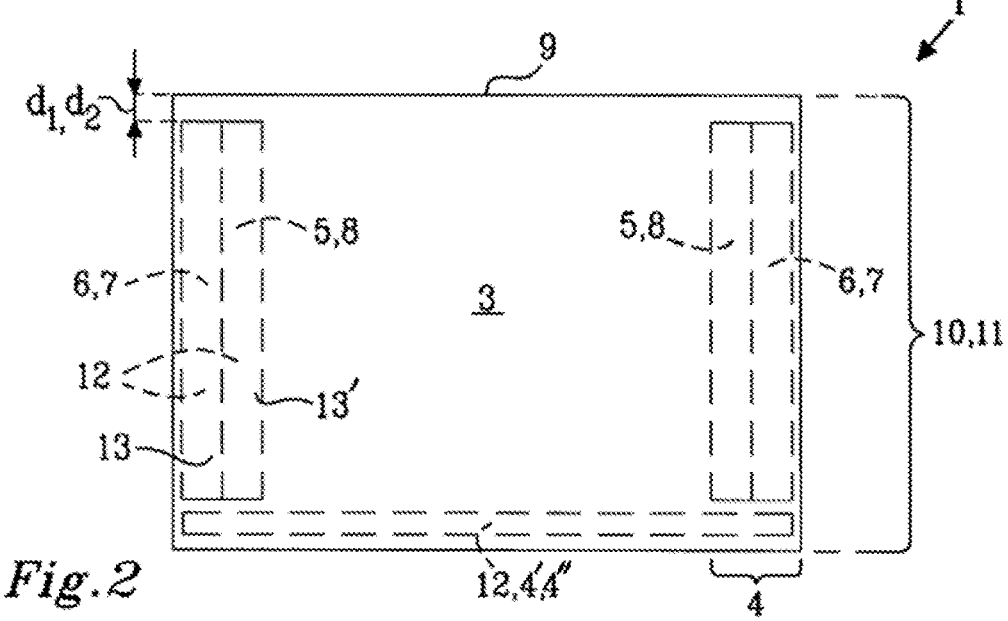
FIG. 2 shows the packaging unit depicted in FIG. 1 in a folded state.

FIG. 1 depicts a packaging unit 1 for hygiene articles according to an embodiment. The packaging unit is formed from a sheet of material having an inner surface 2 and an outer surface 3, the inner surface comprising an edge zone 4 comprising an inner edge portion 5, 8 and an outer edge portion 6, 7. The packaging unit 1 also comprises a first transverse edge zone 4' and a second transverse edge zone 4". The sheet has a first folding axis 9, wherein the folding axis divides the sheet into a first region 10 and a second region 11. As shown in FIG. 1, the outer edge portion 6 of the edge zone 4 of the first region 10 is provided with resealable adhesive 12, thus forming a first adhesive zone 13, while the inner edge portion 5 of the edge zone 4 of the first region 10 is adhesive-free. As may be seen in FIG. 1, the first adhesive zone 13 is arranged at a distance $d_1$ from the first folding axis 9, which provides a sufficient space for a folding tool to be positioned at the first folding axis 9. In the embodiment shown in FIG. 1, the distance $d_1$ is 5 mm. Further, the inner edge portion 8 of the edge zone 4 of the second region 11 is provided with resealable adhesive 12, thus forming a second adhesive zone 13', while the outer edge portion 7 of the edge zone 4 of the second region 11 is adhesive-free. As depicted in FIG. 1, the second adhesive zone 13' is arranged at a distance $d_2$ from the first folding axis 9, the distance $d_2$ being 5 mm. Also, the first transverse edge zone 4' of the first region 10 is provided with resealable adhesive 12, while the second transverse edge zone 4" of the second region 11 is adhesive-free. Thus, the adhesive pattern in the first region 10 is complementary to the adhesive pattern of the second region 11. This in turn means that, when the sheet is folded about the first folding axis 9 as shown in FIG. 2, the edge portions 6 carrying resealable adhesive 12 in the first region 10 are brought in contact with the adhesive-free edge portions 7 in the second region 11, the edge portions 8 carrying resealable adhesive 12 in the second region 11 are brought in contact with the adhesive-free edge portions 5 in the first region 10, and the first transverse edge zone 4' carrying resealable adhesive 12 in the first region 10 is brought in contact with the adhesive-free second transverse edge zone 4" in the second region 11. The space provided by the distances $d_1$ and $d_2$ at each side of the first folding axis 9 ensures facilitated and accurate folding.

Figure 3:
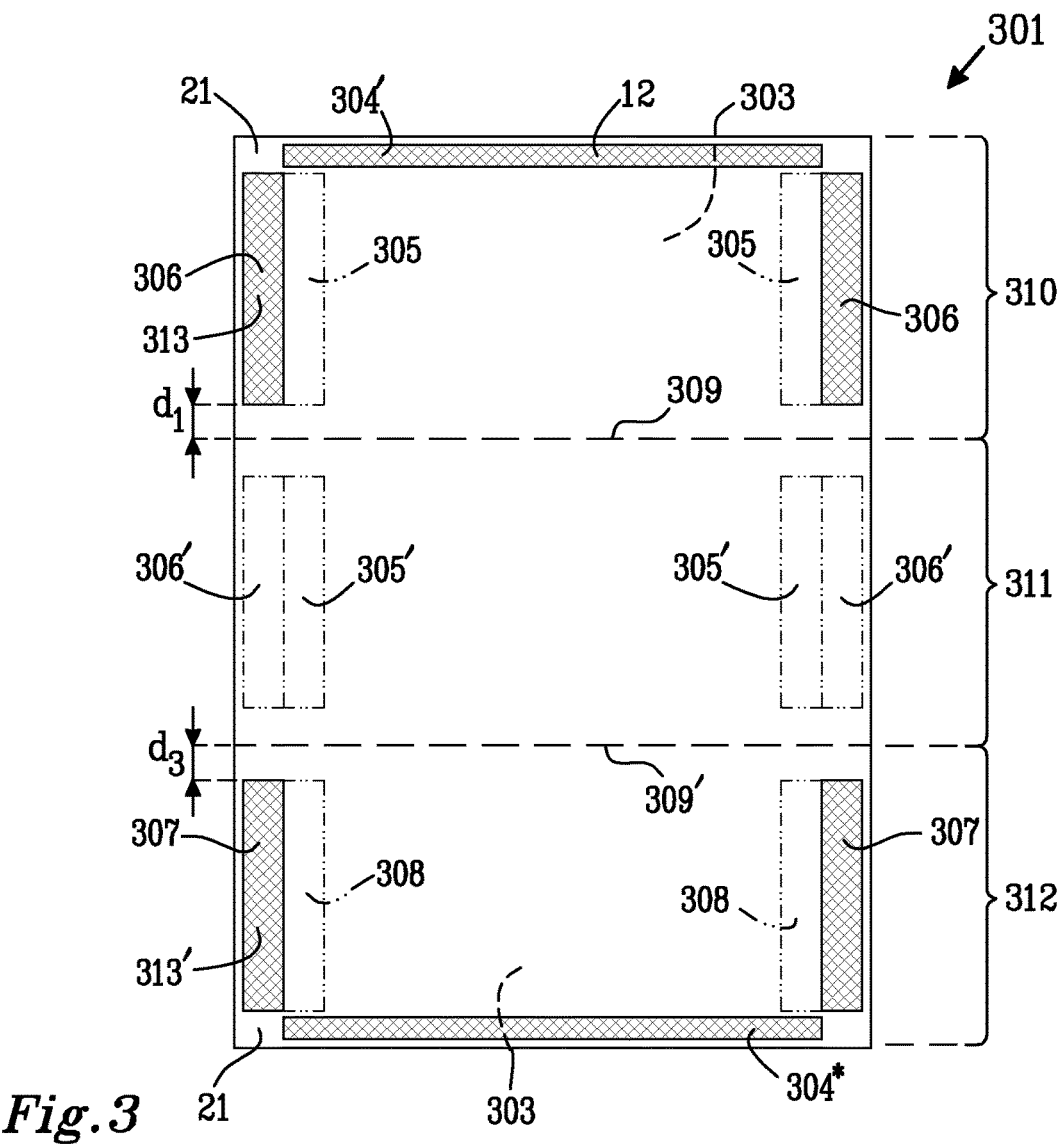
FIG. 3 shows a packaging unit according to an embodiment having two folding axes.
Figure 4:
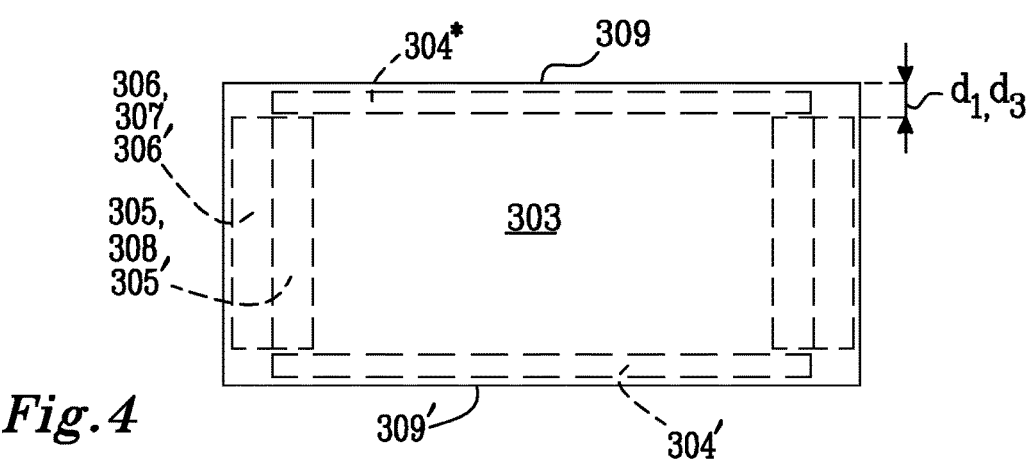
FIG. 4 shows the packaging unit depicted in FIG. 3 in a folded state.

The most common packaging unit for individual packaging of absorbent articles is a rectangular sheet comprising two folding axes, longitudinal edges and transverse edges. Such an embodiment is illustrated in FIG. 3. The packaging unit 301 is a rectangular sheet comprising a first folding axis 309 and a second folding axis 309' dividing the packaging unit into a first region 310, a second region 311 and a third region 312. Each of the regions comprises an inner edge portion 305, 305', 308 and an outer edge portion 306, 306', 307. As shown in FIG. 3, the outer edge portions 306, 307 of the first and third regions respectively are provided with resealable adhesive 12, thus forming a first and a third adhesive zone 313, 313", respectively, while the inner edge portions 305, 308 of the first and third regions respectively are adhesive-free. As may be seen in FIG. 3, the first adhesive zone 313 is arranged at a distance $d_1$ from the first folding axis 309, which provides a sufficient space for a folding tool to be positioned at the first folding axis 309. In the embodiment shown in FIG. 3, the distance $d_1$ is 7 mm. Further, the third adhesive zone 313" is arranged at a distance $d_3$ from the second folding axis 309', the distance $d_3$ being 7 mm. Both the outer edge portion 306' and the inner edge portion 305' of the second region 311 are adhesive-free. This in turn means that, when the sheet is e-folded about the folding axes 309, 309' as shown in FIG. 4, the outer edge portions 306 of the first region 310 or the outer edge portions 307 of the third region 312 carrying resealable adhesive 12 are brought in contact with the adhesive-free outer edge portions 306' in the second region 311, depending on whether the folding is initiated around the first folding axis 309 or the second folding axis 309', and thus on which of the first and the third regions 310, 312 that is brought in contact with the second region 311. It should be noted that the order in which the packaging unit depicted in FIG. 4 is folded is irrelevant. For example, the packaging unit may be folded around the second folding axis 309', bringing the third region 312 in contact with the second region 311, sealing the outer edge portions 307, 306'. The packaging unit is subsequently folded around the first folding axis 309', bringing the first region 310 in contact with the outer surface of the third region 312, thus sealing the packaging unit (FIG. 4). The folding order may also be reversed. This is a great advantage, since when the packaging unit of the present disclosure is used for disposal, the user does not have to fold the packaging unit in any particular order to be able to obtain a tightly sealed package. The packaging unit will provide a sufficiently tight and hygienic package regardless of the folding order.

In order to obtain a tight package, the first and second transverse edge zones 304' and 304* of the packaging unit 301 are provided with resealable adhesive 12. When both transverse edge zones 304' and 304* are provided with resealable adhesive, the folding order is irrelevant, as described above. It is also conceivable to provide only one of the first and the second transverse edge zones 304' and 304* with resealable adhesive. In this case, the folding is to be initiated around the folding axis being positioned closest to the adhesive-free transverse edge zone, such that the region comprising the adhesive-covered transverse edge zone forms a lid and the resealable adhesive positioned at the transverse edge zone seals the packaging unit.

In order to facilitate the opening of the package, the adhesive-covered portions are positioned such that at least one of the corner portions 21 of the packaging unit 301 is adhesive-free, thus forming a gripping tab that is gripped by the user upon opening the package. Moreover, the adhesive-free corner portion 21 serves as an evacuation opening when the packaging unit is sealed (FIG. 4).

It should be noted that when the packaging unit according to the present disclosure is used for disposal, the user can choose to roll up the packaging unit and the soiled article positioned on it rather than folding it.

Although the present disclosure has been described with reference to various embodiments, those skilled in the art will recognise that changes may be made without departing from the scope of the present disclosure. It is intended that the detailed description be regarded as illustrative and that the appended claims including all the equivalents are intended to define the scope of the present disclosure.

The invention claimed is:

1. A packaging unit for hygiene articles, the packaging unit being formed from a sheet of material, said sheet having an inner surface and an outer surface, said inner surface comprising an edge zone comprising an inner edge portion and an outer edge portion, said sheet having at least one first folding axis, said at least one first folding axis dividing said sheet into a first region and a second region, one of said inner edge portion and said outer edge portion of said edge zone of said first region being provided with resealable adhesive, thus forming a first adhesive zone, and the other of said inner edge portion and said outer edge portion of said edge zone of said first region being adhesive-free; and wherein one of said inner edge portion and said outer edge portion of said edge zone of said second region corresponding to an adhesive-carrying edge portion of said first region is adhesive-free, such that when said sheet is folded about said at least one first folding axis (9, 309), said one of the inner edge portion and the outer edge portion carrying the resealable adhesive in said first region is brought in contact with said one of said inner edge portion and said outer edge portion that is adhesive-free in said second region, wherein a distance between said at least one first folding axis and said first adhesive zone is 1-20 mm.

2. The packaging unit according to claim 1, wherein one of said inner edge portion and said outer edge portion of said edge zone of said second region that is complementary to said adhesive-carrying edge portion of said first region is adhesive-free.

3. The packaging unit according to claim 1, wherein one of said inner edge portion and said outer edge portion of said edge zone of said second region that is complementary to said adhesive-carrying edge portion of said first region is provided with resealable adhesive, thus forming a second adhesive zone.

4. The packaging unit according to claim 3, wherein a distance between said at least one first folding axis and said second adhesive zone is 1-20 mm.

5. The packaging unit according to claim 1, wherein said sheet is of substantially rectangular shape and comprises longitudinal edges, a first transverse edge and a second transverse edge, and corner portions, said edge zone of said first region and said edge zone of said second region of said sheet being arranged along said longitudinal edges.

6. The packaging unit according to claim 5, wherein said sheet comprises a first transverse edge zone and a second transverse edge zone, and wherein at least a portion of at least one of said first transverse edge zone and said second transverse edge zone is provided with resealable adhesive.

7. The packaging unit according to claim 6, wherein a portion of said first transverse edge zone of said first region is provided with resealable adhesive, while a remaining portion of said first transverse edge zone of said first region is adhesive-free, and a portion of said second transverse edge zone of said second region is provided with resealable adhesive, while a remaining portion of said second transverse edge zone of said second region is adhesive-free in a complementary manner to said first transverse edge zone of said first region such that when said sheet is folded about said at least one first folding axis, said portion of said first transverse edge zone carrying the resealable adhesive in said first region is brought in contact with said remaining portion of said second transverse edge zone that is adhesive free in said second region, and said portion of said second transverse edge zone carrying the resealable adhesive in said second region is brought in contact with said remaining portion of said first transverse edge zone that is adhesive-free in said first region.

8. The packaging unit according to claim 5, wherein at least one of said corner portions is free from resealable adhesive such that a gripping tab is formed.

9. The packaging unit according to claim 1, wherein said sheet has a first folding axis and a second folding axis, dividing said sheet into said first region, said second region and a third region, wherein one of an inner edge portion and an outer edge portion of an edge zone of said third region is provided with resealable adhesive, thus forming a third adhesive zone.

10. The packaging unit according to claim 3, wherein said sheet has a first folding axis and a second folding axis, dividing said sheet into said first region, said second region and a third region, and wherein an inner edge portion and an outer edge portion of an edge zone of said third region is adhesive-free.

11. The packaging unit according to claim 9, wherein a distance between said second folding axis and said third adhesive zone is 1-20 mm.

12. The packaging unit according to claim 9, wherein said sheet is folded along said first folding axis and said second folding axis with said first region, said second region and said third region in an overlapping configuration.

13. The packaging unit according to claim 9, wherein said sheet comprises a first transverse edge zone and a second transverse edge zone, and wherein at least a portion of at least one of said first transverse edge zone and said second transverse edge zone is provided with resealable adhesive.

14. The packaging unit according claim 1, wherein said sheet is one of opaque and comprising print.

15. The packaging unit according to claim 1, wherein said resealable adhesive is a pressure-sensitive adhesive with essentially unlimited open time.

16. The packaging unit according to claim 1, wherein said packaging unit is reclosable.

17. A method of forming a packaging unit for hygiene articles from a sheet of material, comprising the steps of:
 a. providing a sheet having an inner surface and an outer surface, said inner surface comprising an edge zone comprising an inner edge portion and an outer edge portion, said sheet having at least one first folding axis, said at least one first folding axis dividing said sheet into a first region and a second region;
 b. providing one of said inner edge portion and said outer edge portion of said edge zone of said first region with resealable adhesive, such that the other of said inner edge portion and said outer edge portion of said edge zone of said first region is adhesive-free, thus forming a first adhesive zone; wherein one of said inner edge portion and said outer edge portion of said edge zone of said second region corresponding to an adhesive-carrying edge portion of said first region is adhesive-free; and such that a distance between said at least one first folding axis and said first adhesive zone is 1-20 mm; and
 c. folding the sheet about said at least one first folding axis, such that the one of said inner edge portion and said outer edge portion carrying the resealable adhesive in said first region is brought in contact with the one of said inner edge portion and said outer edge portion that is adhesive-free in said second region.

18. The method according to claim 17, wherein said method further comprises the step of:
 providing one of said inner edge portion and said outer edge portion of said edge zone of said second region complementary to said one of said inner edge portion and said outer edge portion of said edge zone of said first region that is provided with the resealable adhesive, thus forming a second adhesive zone.

19. The method according to claim 18, wherein a distance between said second adhesive zone and said first folding axis is 1-20 mm.

20. The method according to claim 17, wherein said sheet has a first folding axis and a second folding axis dividing said sheet into said first region, said second region and a third region, the third region having an edge zone comprising an inner edge portion and an outer edge portion, the method further comprising the steps of:
 d. providing one of said inner edge portion and said outer edge portion of said edge zone of said third region with resealable adhesive, thus forming a third adhesive zone;
 e. folding the sheet such that the first region, the second region and the third region are arranged in an overlapping configuration.

21. The method according to claim 20, wherein a distance between said third adhesive zone and said second folding axis is 1-20 mm.

* * * * *